United States Patent [19]

Hempel et al.

[11] 3,935,258

[45] Jan. 27, 1976

[54] PROCESS FOR MAKING N-ARYLUREA COMPOUNDS AND HERBICIDAL COMPOSITIONS CONTAINING SAME

[75] Inventors: Jan Hempel, Leverkusen; Erich Klauke, Odenthal-Hahnenberg, both of Germany

[73] Assignee: Bayer Aktiengesellschaft, Leverkusen, Germany

[22] Filed: June 1, 1972

[21] Appl. No.: 258,705

[30] Foreign Application Priority Data

June 12, 1971 Germany............................ 2129200

[52] U.S. Cl.............................. 260/553 A; 71/120
[51] Int. Cl.².................................... C07C 127/19
[58] Field of Search........... 260/553 A; 204/158 HA

[56] References Cited
UNITED STATES PATENTS 3,661,989    5/1972    Nawakowski................... 260/553 A

FOREIGN PATENTS OR APPLICATIONS 1,501,293    10/1967    France............................ 260/553 A

OTHER PUBLICATIONS

Wallis et al., Organic Reactions, Vol. III, J. Wiley & Sons, N.Y., pp. 267–270, (1946).
Bright et al., J. Am. Chem. Soc., Vol. 61, pp. 618–629, (1939).
Renfrow et al., J. Am. Chem. Soc., Vol. 59, pp. 2308–2314, (1937).
Berndt et al., J. Org. Chem., Vol. 31, pp. 976–977, (1966).

*Primary Examiner*—James O. Thomas, Jr.
*Assistant Examiner*—G. Breitenstein
*Attorney, Agent, or Firm*—Burgess, Dinklage & Sprung

[57] ABSTRACT

N-arylurea compounds of the formula

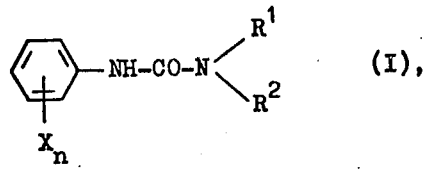

in which
$n$ is 0, 1, 2, 3, 4 or 5,
X is halogen or halomethoxy, the X's being identical or different when $n$ is 2 to 5,
$R^1$ is hydrogen, alkyl of from 1 to 4 carbon atoms, hydroxyalkyl of from 1 to 4 carbon atoms or alkenyl of from 2 to 4 carbon atoms, and
$R^2$ is alkyl of from 1 to 4 carbon atoms, hydroxyalkyl of from 1 to 4 carbon atoms or alkenyl of from 2 to 4 carbon atoms are prepared by reacting an arylcarboxylic acid amide of the general formula

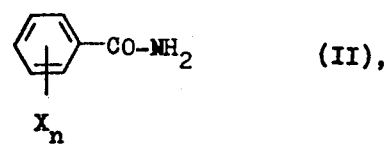

in which
X and $n$ have the meanings stated above, with an alkali metal hypohalite or an alkaline earth metal hypohalite at a temperature of from 0° to 40°C in the presence of water as a diluent, and reacting the resulting aqueous solution with an amine of the general formula

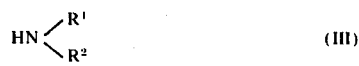

in which
$R^1$ and $R^2$ have the meanings stated above, at an elevated temperature, preferably at a temperature of from 30° to 100°C.

5 Claims, No Drawings

PROCESS FOR MAKING N-ARYLUREA COMPOUNDS AND HERBICIDAL COMPOSITIONS CONTAINING SAME

The present invention relates to a novel process for the preparation of certain N-arylurea compunds. In addition, this invention relates to herbicidal compositions containing such compounds and to their use as herbicides.

It is known that N-aryl-N'-alkylureas can be prepared from arylisocyanates and alkylamines (see, for Example, Houben Weyl, Methoden der organischen Chemie, Vol VIII, page 157). This process is generally used because isocyanates can in many cases be prepared by industrially feasible processes by nitration of substituted aromatics, reduction of the nitro group to give the amino group, and phosgenation of the amines. This process, however, is not usable industrially if the intermediate compounds are difficultly accessible and/ or can only be prepared according to alternative expensive syntheses.

It is also known that phenylurea can be prepared from N-halobenzoic acid amide and aqueous ammonia (J. Chem. Soc. (London) 121, 205 (1922). This process, however, has not found acceptance in industry, since reactions with N-haloamides should only be carried out in small batches (see Houben Weyl, Methoden der organischen Chemie, Vol. 5/3, page 807 (1962) and the process offers no advantage over the usual reaction of phenylisocyanate with ammonia.

The present invention provides a process for the preparation of an N-arylurea of the general formula

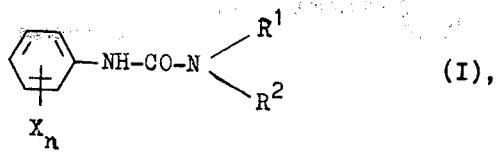

in which,
n is 0, 1, 2, 3, 4 or 5,
X is halogen or halomethoxy, the X's being identical or different when n is 2 to 5,
$R^1$ is hydrogen, alkyl of from 1 to 4 carbon atoms, hydroxyalkyl of from 1 to 4 carbon atoms or alkenyl of from 2 to 4 carbon atoms, and
$R^2$ is alkyl of from 1 to 4 carbon atoms, hydroxyalkyl of from 1 to 4 carbon atoms or alkenyl of from 2 to 4 carbon atoms, which process comprises reacting an arylcarboxylic acid amide of the general formula

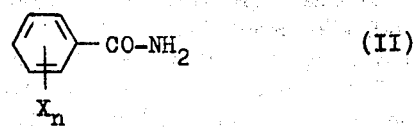

in which
X and n have the meanings stated above, with an alkali metal hypohalite or an alkaline earth metal hypohalite (prepared from an alkali metal or alkaline earth metal hydroxide and a halogen) at a temperature of from 0° to 40°C in the presence of water as a diluent, and reacting the resulting aqueous solution with an amine of the general formula

in which
$R^1$ and $R^2$ have the meanings stated above, at an elevated temperature, preferably at a temperature of from 30° to 100°C.

It is surprising that, in light of the particularly simple manner in which the process according to the invention may be effected with the use of cheap and non-dangerous auxiliary materials and diluents, very good yields with high purity can be attained.

The process according to the invention exhibits a number of particular advantages. Thus, the starting materials required in this process for the preparation of the ureas of the general formula (I) above can be prepared (in good yield) according to industrially favorable processes.

In contrast, for the preparation of isocyanates that could serve as starting materials for the preparation of the ureas of the general formula (I), no industrially usable process is known. In order to be able to prepare, for example, 4-trifluoromethoxyphenylisocyanate or 3-chloro-4-trifluoromethoxyphenylisocyanate, 4-trifluoromethoxybenzene or 3-chloro-4-trifluoromethoxybenzene must be nitrated, reduced to give the corresponding aniline, and then phosgenated. These two trifluoromethoxybenzene derivatives, however, cannot be prepared in a simple, industrially advantageous manner by fluorination of the corresponding trichloromethoxybenzene compounds, since trichloroanisole is not preparable by side-chain chlorination of anisole (see J. Appl. Chem. 3, 409 (1953) and o-chlorotrichloromethoxybenzene can be coverted into o-chlorotrifluoromethoxybenzene only in poor yields (Zh. Obshchei Khim. 27, 518 (1957). Furthermore, in the nitration of di-substituted benzenes, several isomers occur, which lead to inhomogeneous reaction products (J. Gen. Chem. USSR (Engl.) 27 587, (1957).

On the other hand, the carboxylic acid amides used in the process according to the present invention can be prepared free from isomers. The process according to this invention therefore represents an enrichment of the art.

If 4-trifluoromethoxybenzoic acid amide, sodium hypochlorite and dimethylamine are used as starting materials, the reaction can be represented by the following equation:

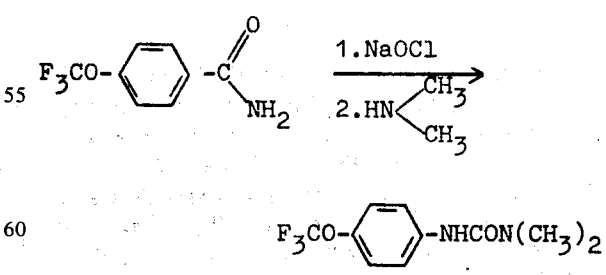

A number of the starting materials of the formula (II) are known (see, for example, J. Gen. Chem. USSR (Engl.) 27, 587 (1957). The compounds that have not hitherto been described in the literature can be prepared according to a process that does not belong to the prior art.

Thus, 3-chloro-4-trifluoromethoxybenzoic acid amide is prepared by first reacting 4-trichloromethoxybenzoic acid chloride with chloride with chlorine to give 3-chloro-4-trichloromethoxybenzoic acid chloride and reacting this with anhydrous hydrofluoric acid and antimony pentachloride as a catalyst at an elevated temperature, preferably at a temperature between 120° and 150°C, and at a pressure between 10 and 30 atmospheres, to give 3-chloro-4-trifluoromethoxybenzoyl fluoride. A particularly simple embodiment of this process consists in preparing (by the action of thionyl chloride on 4-methoxybenzoic acid) 4-methoxybenzoyl chloride, converting the last-mentioned compound (without isolating it) at an elevated temperature in the same apparatus by action of chlorine in the presence of a radical-forming agent, such as ultra-violet light or a peroxide, to give 4-trichloromethoxybenzoyl chloride and, from the last-mentioned compound, preparing 3-chloro-4-trichloromethoxybenzoyl chloride by further action of chlorine in the same apparatus in the presence of a nuclear chlorination catalyst, such as antimony pentachloride. This intermediate compound reacts, with further use of the catalyst, with hydrofluoride acid under the above-mentioned conditions to give 3-chloro-4-trifluoromethoxybenzoyl fluoride, which can, in a known manner, be converted with aqueous ammonia into the corresponding benzoic acid amide. The reaction course described above can be represented by the following set of equations:

metal hydroxide, such as calcium hydroxide or barium hydroxide, and a halogen, such as chlorine or bromine. Preferably, a sodium-hydroxide-alkaline hypochlorite solution (sodium hypochlorite solution) is used.

Water is used as the diluent in the process according to the invention.

The reaction temperatures can be varied within a fairly wide range. The reaction temperature, until dissolution of the arylcarboxylic acid amide in the alkaline hypochlorite solution, is kept at from 0° to 40°C, preferably at from 20° to 30°C. After addition of the amine, the work is carried out at from 30° to 100°C, preferably at from 50° to 70°C.

When carrying out the process according to the invention, approximately equimolar amounts of arylcarboxylic acid amide of the formula (II), alkali metal hypohalite (or alkaline earth metal hypohalite) and amine of the formula (III) are generally used, but an excess of the amine is not detrimental. The ureas of the formula (I) are only sparingly soluble in water and are obtained as crystallized solid products; they can be isolated and purified in any customary manner.

The following Examples are illustrative.

EXAMPLE 1

Preparation of N-4-trifluoromethoxy-phenyl-N',N'-dimethylurea

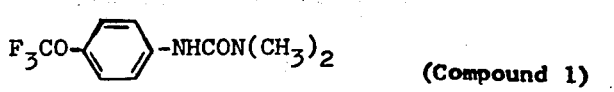
(Compound 1)

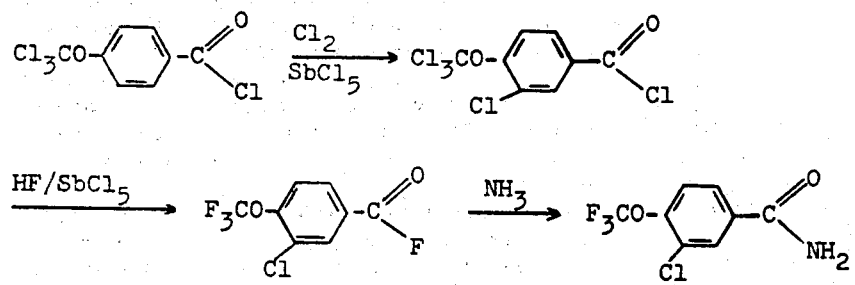

As example of the acid amides of the formula (II) to be used according to the invention, there may be mentioned 4-trifluoromethoxybenzoic acid amide and 3-chloro-4-trifluoromethoxybenzoic acid amide.

The amines to be used as starting materials are defined generally by the formula (III). Particularly suitable amines are methylamine, dimethylamine, methylethylamine, n-propylamine, isopropylamine, n-butylamine, sec-butylamine, methyl-n-butylamine and diethanolamine.

The alkali metal hypohalite solutions or alkaline earth metal hypohalite solutions are expediently freshly prepared from alkali metal hydroxide, such as sodium hydroxide or potassium hydroxide, or alkaline earth 1000 ml of a sodium hypochlorite solution, prepared from 300 g of sodium hydroxide and 152 g of chlorine, were added to 430 g of 4-trifluoromethoxybenzoic acid amide in 2000 ml of water. The temperature was kept at 25°C. When all had dissolved, 200 ml of a 40 – 50% – strength aqueous dimethylamine solution were added and heating to 60° –80°C was effected for ½ to 1 hour. The urea precipitates, was filtered off with suction and can be purified by dissolving in methanol and precipitation with water. There were obtained 363 g of N-4-trifluoromethoxyphenyl-N',N'-dimethylurea; m.p. 132° – 134°C.

In an analogous manner, the following compounds could also be prepared:

Table

| Compound No. | Active compound | Melting point (°C) |
| --- | --- | --- |
| 2) | F$_3$CO—⟨C$_6$H$_3$(Cl)⟩—NHCON(CH$_3$)$_2$ | 123 – 124 |
| 3) | F$_3$CO—⟨C$_6$H$_3$(Cl)⟩—NHCONHCH$_3$ | 134 – 138 |
| 4) | F$_3$CO—⟨C$_6$H$_3$(Cl)⟩—NHCONHC$_3$H$_7$-n | 125 |
| 5) | F$_3$CO—⟨C$_6$H$_3$(Cl)⟩—NHCON(CH$_2$CH$_2$OH)$_2$ | 112 – 114 |
| 6) | ⟨C$_6$H$_5$⟩—NHCON(CH$_3$)$_2$ | 134 |

The arylcarboxylic acid amides used as starting materials can be illustratively prepared as follows:

(a) 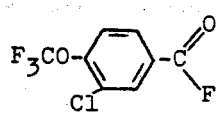

230 g of p-anisic acid and 230 g of thionyl chloride were gradually warmed to 60°C under nitrogen. The reaction mixture was stirred at 60°C for 10 hours. Thereafter, excess thionyl chloride was drawn off in a vacuum. The product remaining behind was chlorinated at 150°C and under irradiation with ultraviolet light. The reaction temeprature was then elevated to 190° to 200°C, and the chlorination reaction was completed after about 5 hours. To the product remaining behind there were added 5 g of antimony pentachloride. At 80° – 100°C, chlorine was introduced until the calculated amount (1 mole equivalent) had been taken up. 453 g of crude product were obtained; $n_D^{20}$ = 1.5825. The crude procuct was added to 500 ml of anhydrous hydrofluoric acid in a steel autoclave and heated to 140°C, with stirring. The hydrogen chloride formed was released at about 20 atmospheres gauge. After cessation of evolution of gas, the product was distilled in a vacuum: b.pt: 76° – 79°C/14 mm Hg.

300 g of 3-chloro-4-trifluoromethoxybenzoic fluoride were obtained; $n_D^{20}$ = 1.4545.

(b) 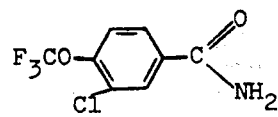

400 g of chloro-4-trifluoromethoxybenzoyl fluoride were added dropwise at room temperature, with cooling, to 1400 ml of semi-concentrated ammonia solution. After completion of the reaction, suction filtration was effected and the residue on the filter was washed until neutral.

373 g of 30 chloro-4-trifluoromethoxybenzoic acid amide were obtained, m.p.: 100° – 102°C.

The N-aryl-N'-alkylureas of the formula (I) that can be prepared by the process according to the invention from arylcarboxylic acid amides and alkylamines are known as active compounds with herbicidal effectiveness and can therefore be used as weedkillers. See, for instance, German Published Specification (DOS) No. 1 909 521.

The active compounds according to the present invention can be coverted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents. In the case of the use of water as an extender, organic solvents can, for example, also be used as auxiliary solvents.

As liquid diluents, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulofixide or acetonitrile, as well as water.

By liquiefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates; and preferred examples of dispersing agents include lignin, sulfite waste liquors and methyl cellulose.

The active compounds according to the invention can be present in the formulations as a mixture with other active substances.

The formulations, in general, contain from 0.1 to 95, preferably from 0.5 to 90, percent by weight of active compound.

The active compounds can be used as such, in the form of their formulations or in the form of the application forms prepared therefrom, such as ready-to-use solutions, emulsions, suspensions, powders, pastes and granules. They may be employed in any customary manner, for example by watering, spraying, atomising, sprinkling or dusting.

The amounts of active substance employed can vary over a fairly wide range; it depends essentially on the nature of the desired effect. In general, however, the amounts used are from 0.15 to 15 kg/hectare, preferably from 0.5 to 10 kg/hectare.

The present invention thus also provides a herbicidal composition containing as active ingredient an N-arylurea prepared according to the present invention in admixture with a solid or liquefied gaseous diluent or carrier or in admixture with a liquid diluent or carrier containing a surface-active agent.

The present invention also provides a method of combating weeds which comprises applying to the weeds or a weed habitat an N-arylurea prepared according to the present invention alone or in the form of a composition containing as active ingredient such as N-arylurea in admixture with a diluent or carrier.

The process according to the invention can be used not only for the preparation of the ureas of the formula (I) but quite generally for the preparation of ring-unsubstituted and ring-substituted N-arylureas. Unsuitable as starting materials are only those benzoic acid amides that contain, as ring substituents, groups sensitive to alkaline hypohalite solutions, such as formul or amino groups. Such groups can, however, be reacted with suitable reactants and thereby be protected against alkaline hypohalite solutions, the original substituents being regenerated after the main reactions. The process is, however, particularly advantageous industrially for the production of N-arylureas of the formula (I).

It will be understood that the specification and examples are illustrative but not limitative of the present invention and that other embodiments within the spirit and scope of the invention will suggest themselves to those skilled in the art.

What is claimed is:

1. Process for the preparation of a substituted N-phenyl-urea compound of the formula

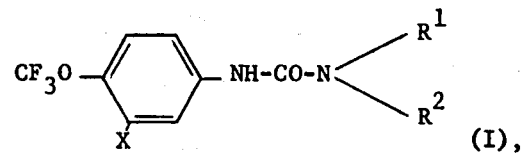

wherein
X is hydrogen or chlorine;
R¹ is hydrogen, methyl or β-hydroxyethyl, and
R² is alkyl with 1 to 3 carbon atoms or β-hydroxyethyl
which process comprises reacting in substantially equimolar amounts an substituted benzoic acid amide of the formula

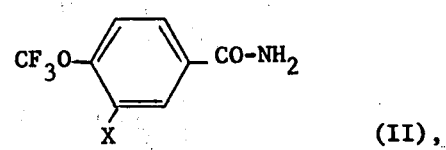

in which
X is defined as above,
with an alkali metal hypohalite or an alkaline earth metal hypohalite at a temperature of from 0° to 40°C in the presence of water as a diluent, and adding to the resulting aqueous solution an amine of the general formula

in which
R¹ and R² have the meanings stated above, and then reading at an elevated temperature of 50°– 70°C.

2. Process as claimed in claim 1 wherein said hypohalite is prepared from an alkali metal or alkaline earth metal hydroxide and a halogen.

3. Process as claimed in claim 1 wherein the hypohalite is freshly prepared, aqueous sodium hypochlorite.

4. Process as claimed in claim 1 wherein the arylcarboxylic acid amide (II) is 4-trifluoromethoxy-benzoic acid amide.

5. Process as claimed in claim 1 wherein the arylcarboxylic acid amide is 3-chloro-4-trifluoromethoxybenzoic acid amide having the formula

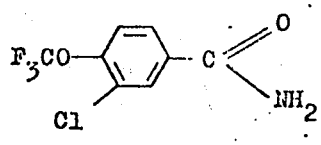

* * * * *

UNITED STATES PATENT OFFICE
CERTIFICATE OF CORRECTION

PATENT NO. : 3,935,258
DATED : January 27, 1976
INVENTOR(S) : Jan Hempel et al

It is certified that error appears in the above-identified patent and that said Letters Patent are hereby corrected as shown below:

Column 5, line 54, correct spelling of "product".

Column 8, Claim 1, line 43, cancel "reading" and substitute -- reacting --.

Signed and Sealed this

Fifth Day of October 1976

[SEAL]

Attest:

RUTH C. MASON
Attesting Officer

C. MARSHALL DANN
Commissioner of Patents and Trademarks